(12) United States Patent
Schumacher et al.

(10) Patent No.: US 9,687,578 B2
(45) Date of Patent: *Jun. 27, 2017

(54) STERILANT CHALLENGE DEVICE

(71) Applicant: 3M INNOVATIVE PROPERTIES COMPANY, St. Paul, MN (US)

(72) Inventors: Knut Schumacher, Neuss (DE); Robbert-Jan Hermsen, Steijl (NL); Anton Kuepper, Kaarst (DE)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 92 days.

This patent is subject to a terminal disclaimer.

(21) Appl. No.: 14/428,457

(22) PCT Filed: Sep. 18, 2013

(86) PCT No.: PCT/US2013/060346
§ 371 (c)(1),
(2) Date: Mar. 16, 2015

(87) PCT Pub. No.: WO2014/047139
PCT Pub. Date: Mar. 27, 2014

(65) Prior Publication Data
US 2015/0231294 A1 Aug. 20, 2015

(30) Foreign Application Priority Data
Sep. 18, 2012 (GB) .................................. 1216588.2

(51) Int. Cl.
*A61L 2/28* (2006.01)

(52) U.S. Cl.
CPC ..................................... *A61L 2/28* (2013.01)

(58) Field of Classification Search
CPC ........................................................ A61L 2/28
(Continued)

(56) References Cited

U.S. PATENT DOCUMENTS 3,479,131 A     11/1969   Scoffield et al.
3,834,448 A  *  9/1974   Cooksley .................. C02F 1/04
                                                                165/154

(Continued)

FOREIGN PATENT DOCUMENTS

DE     25 58 936      7/1977
DE     36 36 716      5/1988

(Continued)

OTHER PUBLICATIONS

Reay et al., Heat pipes: theory, design, and applications, 2014, Elsevier, 6th Ed., p. 239.*

(Continued)

*Primary Examiner* — Kevin Joyner
*Assistant Examiner* — Holly Mull

(57) ABSTRACT

Sterilant challenge device for use in steam sterilizers are described, including devices suitable for determining the efficacy of the non-condensable gas removal stage of a sterilization cycle and/or the quality of steam sterilant in relation to its content of non-condensable gas(es) are disclosed. Sterilant challenge devices having a metal tube having a defining a free space which is open at one end for the entry of sterilant and closed at the other end and at least one thermal load located around the tube are also described.

28 Claims, 2 Drawing Sheets

(58) Field of Classification Search
USPC .......................................................... 422/28
See application file for complete search history.

(56) References Cited

U.S. PATENT DOCUMENTS

| | | | |
|---|---|---|---|
| 4,865,814 A | 9/1989 | Childress | |
| 5,066,464 A * | 11/1991 | Augurt | A61L 2/28 422/414 |
| 6,630,352 B1 * | 10/2003 | Reiner | A61L 2/28 116/216 |
| 2002/0034823 A1 * | 3/2002 | Kuepper | A61L 2/24 436/1 |
| 2003/0087441 A1 | 5/2003 | Lemus et al. | |
| 2003/0162243 A1 * | 8/2003 | Foltz | A61L 2/28 435/31 |
| 2005/0260760 A1 | 11/2005 | Hucker | |
| 2007/0008160 A1 * | 1/2007 | Nagai | A61B 1/00057 340/610 |
| 2010/0036357 A1 * | 2/2010 | Bala | A61L 2/28 604/404 |
| 2010/0218933 A1 * | 9/2010 | Deacon | F24D 1/02 165/285 |
| 2011/0243181 A1 | 10/2011 | Martel | |

FOREIGN PATENT DOCUMENTS

| | | |
|---|---|---|
| DE | 199 44 847 | 5/2001 |
| DE | 20 2006 006 926 | 8/2006 |
| EP | 0 628 814 | 12/1994 |
| EP | 0 776 669 | 6/1997 |
| EP | 0 841 069 | 5/1998 |
| EP | 0 890 833 | 1/1999 |
| EP | 1 230 936 | 8/2002 |
| WO | WO 93/21964 | 11/1993 |
| WO | WO 97/12637 | 4/1997 |
| WO | WO 99/32159 | 7/1999 |
| WO | WO 99/32160 | 7/1999 |

OTHER PUBLICATIONS

Lyons, Materials for architects and builders, 2014, Routledge, 5th Ed., p. 406.*

Lide, CRC handbook of chemistry and physics, 2005, CRC Press, p. 4-135.*

* cited by examiner

US 9,687,578 B2

STERILANT CHALLENGE DEVICE

CROSS REFERENCE TO RELATED APPLICATIONS

This application is a national stage filing under 35 U.S.C. 371 of PCT/US2013/060346, filed Sep. 18, 2013, which claims priority to United Kingdom Application No. 1216588.2, filed Sep. 18, 2012, the disclosure of which is incorporated by reference in their entirety herein.

FIELD

The present disclosure relates to a sterilant challenge device for use in a steam sterilizer for determining the efficacy of the non-condensable gas removal stage of a sterilization cycle andor the quality of steam sterilant.

BACKGROUND

A sterilization process carried out in a sterilization chamber of a sterilizer and used to sterilize medical and hospital equipment is only effective if a certain combination of environmental conditions is achieved within the sterilization chamber of the sterilizer. For example, when steam is used as a sterilant, the object of the sterilization process is to bring steam of a suitable quality and at an appropriate temperature into contact with all surfaces of the articles being sterilized for an appropriate length of time. In some steam sterilizers the process of sterilization is typically conducted in three main phases of a sterilization cycle. In the first phase, air trapped within the article(s) being sterilized (i.e. the load being processed) is removed. The second phase is a sterilizing stage, in which the load is subjected to steam under pressure for a recognised combination of time and temperature, which is known to effect proper sterilization. The third phase is a drying phase in which condensate formed during the first two phases is removed by evacuating the chamber.

Air removal from the sterilization chamber may be achieved in a number of ways. For example, in a gravity steam sterilizer, the principle of gravity displacement is utilized, in which steam entering at the top of the chamber displaces the air which exits through a valve in the base of the chamber. In a prevacuum-type steam sterilizer, on the other hand, air is removed forcibly by deep evacuation of the chamber or by a combination of evacuation and steam injection at either subatmospheric andor superatmospheric pressures.

Any air which is not removed from the sterilization chamber during the air removal phase of the cycle or which leaks into the chamber during a subatmospheric pressure stage due to, e.g., faulty gaskets, valves or seals, may form air pockets within the load that is being sterilized. Likewise, any non-condensable gases (which, in the context of the present disclosure, means gases having a boiling point below that of the sterilant) that are present in the sterilization chamber or are carried within steam supplied to the chamber may form gas pockets within the load. These air or gas pockets will create a barrier to steam penetration, thereby preventing adequate sterilizing conditions being achieved for all surfaces of the load. This is particularly true when porous materials such as hospital linens or fabrics are being sterilized since the air or gas pockets prohibit the steam from penetrating to the interior layers of such materials.

As a result, proper sterilization may not occur. Therefore, there is a need for devices which are capable to determine the efficacy or effectiveness of sterilization cycles and, in particular, to determine the efficacy of the non-condensable gas removal stage of a sterilization cycle andor the quality of steam sterilant.

One commonly-used procedure for evaluating the effectiveness of air removal during the air removal phase of a porous load steam sterilization cycle andor for testing for the presence of non-condensable gases is known as the Bowie-Dick test. The typical Bowie-Dick test pack essentially consists of a stack of freshly laundered towels folded to a specific size, with a chemical indicator sheet placed in the centre of the stack. Chemical indicator test sheets undergo a visible change from one distinct colour to another, for example, from an initial white to a final black colour, upon exposure to the sterilization process. If the air removal within the sterilizer is insufficient, or if non-condensable gases are present during the process in sufficient quantity, an airgas pocket will form in the centre of the stack thereby preventing steam from contacting the steam sensitive chemical indicator test sheet. The consequence of inadequate steam penetration is a non-uniform colour development across the surface of the chemical indicator test sheet: thus, the presence of the airgas pocket will be recorded by the failure of the indicator to undergo the complete or uniform colour change indicative of adequate steam penetration.

Biological indicators can also be used to provide information on the effectiveness of a sterilization cycle. Parametric monitoring has also been used to either monitor or control a sterilization cycle to ensure that proper sterilization conditions are attained. For example, in U.S. Pat. No. 4,865,814 an automatic sterilizer is disclosed which includes a microprocessor which monitors both the temperature and pressure levels inside the sterilization chamber and controls a heater to allow both pressure and temperature to reach predetermined levels before starting a timer. Once the timer is started, it is stopped if the pressure or temperature levels drop below a predetermined minimum. Since it is known that the pressure and temperature variables of saturated steam are mutually dependent variables when saturated steam is enclosed in a sealed chamber, monitoring of these two variables can ensure that proper conditions are maintained during the sterilization cycle.

Although it is desirable to monitor environmental conditions within the sterilization chamber itself, it is generally considered more desirable to be able to monitor the environmental conditions within an actual load being sterilized or within a test pack (such as the Bowie-Dick test pack) that represents such a load. However, the typical Bowie-Dick test pack presents many disadvantages. Since the Bowie-Dick test pack is not preassembled, it must be constructed every time the procedure is used to monitor sterilizer performance. The preparation, assembly and use of the Bowie-Dick test pack is time consuming and cumbersome and, moreover, varying factors, such as laundering, pre-humidification, towel thickness and wear, and the number of towels used, alter the test results.

Therefore, alternative sterilizer testing systems have been developed to overcome these limitations. For example, WO 9712637 describes a sterilant challenge device for use in a sterilizer for determining the efficiency of the air removal stage of a sterilization cycle. The device comprises a tube of thermally-insulating material, the bore of the tube defining a free space which is open at one end for the entry of sterilant and is closed at the other end; a plurality of thermally-conductive masses located around the tube, along the length of the latter, the masses being thermally-separated from one another; and a thermal insulation surrounding the tube and the thermally-conductive masses, whereby the penetration of sterilant along the bore of the tube during a sterilization cycle is inhibited through the accumulation of air and/or non-condensable gas within the free space resulting from the condensation of moisture on the walls of the bore.

The thermally-insulating material suggested by WO 97/12637 is a tube made of Liquid Crystal Polymer (LCP), preferably of a complete aromatic copolyester with a 25% by weight graphite content. Despite the fact that such LCP tubes can be desirably optimized for commercial use, they are not perfect. For example, since the LCP tube is typically die cast it exhibits an anisotropic thermal conductivity: the thermal conductivity along the longitudinal axis of the LCP tube is larger than along a radial direction. This may distort the results since the temperature at a given location of the tube does thus not only depend on the steam temperature at said location but also on the heat transport from a longitudinally displaced location along the tube to said location. Moreover, LCP is more difficult to handle than other materials. In particular, with LCP it is extremely difficult to reliably provide a high level of reproducibility of the test results. Finally, the rates of expansion/contraction of LCP on the one hand and of the thermally conductive material of the thermally conductive masses on the other hand are quite different. Thus, a relatively complex design of the thermally conductive masses is needed in order to accommodate these different rates of expansion/contraction. Typically, said design consists of two halves being held together by two spring clips.

SUMMARY

Accordingly, there is an ongoing need for an improved sterilant challenge device for use in a steam sterilizer which overcomes the above-mentioned drawbacks of the prior art.

The present disclosure provides a sterilant challenge device for use in a steam sterilizer for determining the efficacy of the non-condensable gas removal stage of a sterilization cycle and/or the quality of steam sterilant in relation to its content of non-condensable gas/gases. In the context of the present disclosure, the term "non-condensable gas" generally encompasses a gas consisting of several fractions of different gases and refers to gases having a boiling point below that of the sterilant. The device comprises a metal tube having an inner bore, the bore of the tube defining a free space which is open at one end for the entry of sterilant and closed at the other end; and one or a plurality of thermal loads located around the tube.

It has surprisingly turned out that a tube made from metal is by far superior to the known LCP tubes. Even though the thermal conductivity of most metals is larger than that of LCP, it has been found that the overall heat transfer is advantageously favourable. Moreover, most material properties, in particular the thermal conductivity, of metal are more isotropic than those of die cast LCP. Thus, the heat transfer along the longitudinal axis of the tube, which is considered to be a decisive feature, may even be smaller in case of a metal tube than in case of an LCP tube. Furthermore, if desired and/or needed, the overall heat transfer may be easily and sufficiently optimized, for example by adjusting the wall thickness of the metal tube. In addition, most metals are relatively inexpensive and easy to handle. In particular, a high level of reproducibility may be reliably achieved with metal tubes without any difficulties.

In preferred embodiments, metal tubes have a thermal conductivity of 30 $Wm^{-1}K^{-1}$ (Watt per meter Kelvin) or less, preferably of 25 $Wm^{-1}K^{-1}$ or less, more preferably of 20 $Wm^{-1}K^{-1}$ or less. Thus, such thermal conductivities facilitate minimization or elimination of artefacts due to heat transfer along the length of the metal tube.

It is further preferred that metal tubes have a thermal conductivity greater than 2 $Wm^{-1}K^{-1}$, more preferably greater than 4 $Wm^{-1}K^{-1}$. Here, such thermal conductivities favourably facilitate transport the heat generated during condensation to the thermal loads in a radial direction.

Preferably, metal tubes have a length of 15 cm or less, more preferably 12 cm or less, even more preferably 10 cm or less.

Favourably, metal tubes are hollow cylinders having a wall thickness of 2 mm or less, preferably of 1.5 mm or less, more preferably of 1 mm or less and most preferably of 0.5 mm or less.

Favourably, metal tubes have a bore diameter of between 2 mm and 12 mm, preferably between 3.5 mm and 10.5 mm, more preferably between 5 mm and 8 mm (inclusive the end points).

Favourably, metal tubes inclusive wall thickness and bore may have a cross sectional area of 210 $mm^2$ or less, more preferably of 170 $mm^2$ or less, even more preferably of 140 $mm^2$ or less.

Preferably, the material properties, in particular the thermal conductivity, of metal tubes are essentially isotropic. It is preferred that the thermal conductivity along the longitudinal axis of the tube does not exceed 120%, preferably 110%, and more preferably 105% of the thermal conductivity in a radial direction.

Preferably, metal tubes comprise one or a combination of: stainless steel; non-rusting steel; CrNi-containing steel; titanium; and titanium alloys.

Load(s) preferably have a bore. Desirably the size and shape of the bore of the load(s) generally corresponds to the outer size and shape of the metal tube. This facilitates the provision of a well-defined heat transfer between the tube and the one or more loads. Preferably, the bore of the one or a plurality of loads and/or the surface of the bore of the one or a plurality of loads may be shaped such as to only intermittently contact the metal tube. This desirably allows for an increased control and optimization of the amount of heat transfer between the tube and the load(s). For example, the surface of the bore of the one or more loads may comprise at least one laterally or longitudinally extending groove, preferably at least two or more laterally and/or longitudinally extending grooves, which are preferably spaced equidistantly from each other. In essence, heat transfer then only takes place at the intermittent contact between the load(s) and the tube where no groove is present.

Alternatively or in addition, a foil or sheet of thermally insulating material may be provided between the tube and the one or more loads. Such a foil or sheet may preferably comprise a material comprises one or a combination of: polyester, polypropylene, polyacrylonitrile, Kapton, polyurethane, polyamide, polyimide, polyether imide, PTFE, polyvinylchloride, polycarbonate, epoxy resin, polymethylmethacrylate, polyethylene, and polystyrene. The use of such foils or sheets further aids in providing a well-defined heat transfer between the tube and the one or more loads and/or in controlling or optimizing the amount of heat transfer between the tube and the one or more loads. Foils or sheets preferably comprises a material having a thermal conductivity which is lower than that of the tube. Such materials may have a thermal conductivity of 5 $Wm^{-1}K^{-1}$ or less, more preferably of 1 $Wm^{-1}K^{-1}$ or less. To adjust thermal coupling between the tube and the one or more loads foils or sheets may favorably comprise several holes and/or cut-outs.

Load(s) preferably have a shape substantially corresponding to a cylinder, in particular a cylinder with a bore. In preferred embodiments, the cylinder of the one or more loads comprises a radial slit extending from the outer surface of the cylinder to the bore of the cylinder. Such a radial slit to the bore may ease mounting of a load about a tube. In addition or alternatively thereto, the cylinder of the one or more loads may desirably comprises at least one radial slit extending from the outer surface of the cylinder towards (but not reaching) the bore of the cylinder or preferably at least two radial slits. For embodiments including two more radial slits desirably they are spaced equidistantly from each other. Radial slits may advantageously increase the flexibility of the load(s), since the cylinder material may flex by compressing the one or more slits. Thus, different rates of expansioncontraction may be desirably accommodated.

Load(s) preferably have a heat capacity at 25° C. of equal to or greater than 0.5 $Jg^{-1}K^{-1}$, more preferably of equal to or greater than 0.7 $Jg^{-1}K^{-1}$, even more preferably of equal to or greater than 0.85 $Jg^{-1}K^{-1}$.

It is preferred that the one or more loads comprise aluminium or are made of aluminium.

According to preferred embodiments, the open end of the metal tube is tapered. This may ease the removal of condensed steam within the bore of the tube.

Preferred embodiments of the present disclosure are further elucidated with respect to the following Figures.

Figure 1:
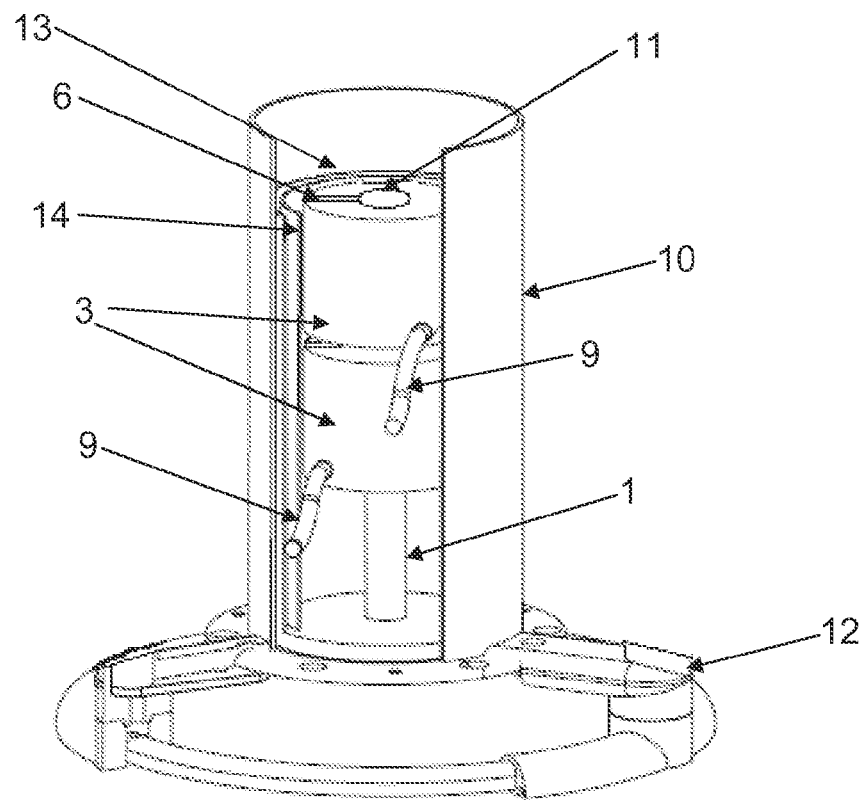
FIG. 1 shows a perspective, partial cross-sectional view of an exemplary embodiment of a sterilant challenge device according to the present disclosure.
Figure 2:
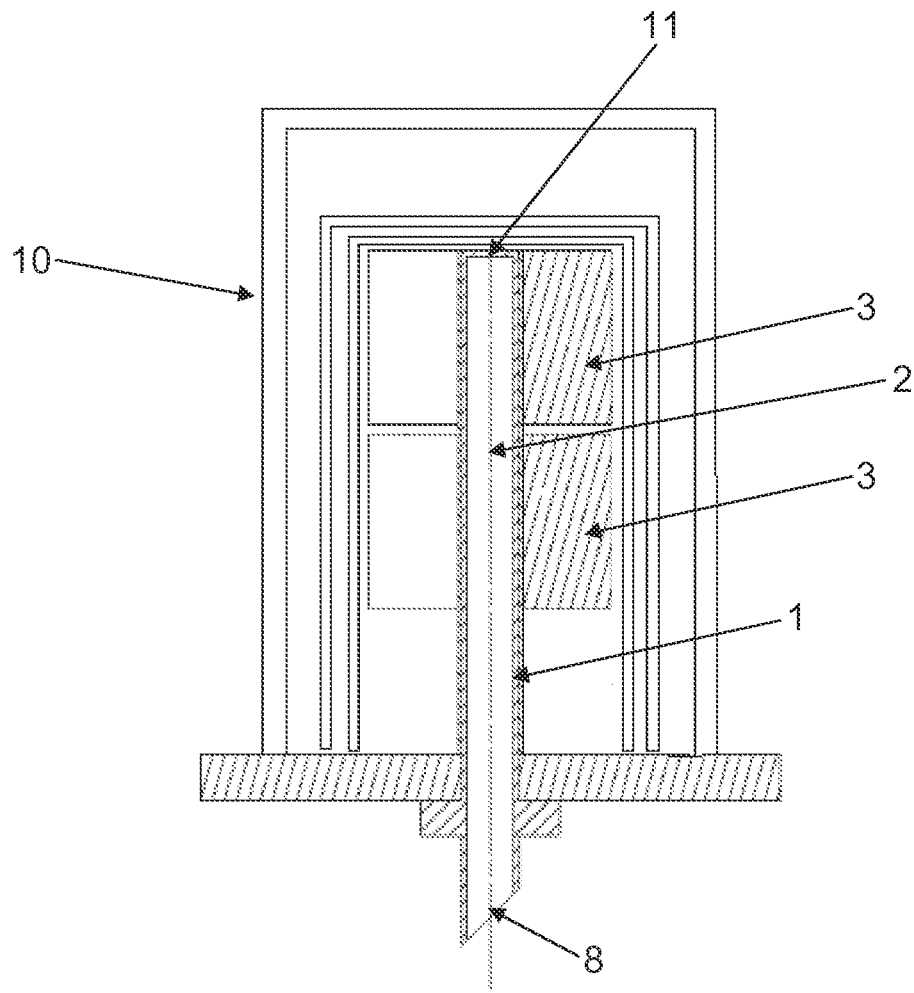
FIG. 2 shows a partial cross-sectional side view of the embodiment shown in FIG. 1.

FIG. 1 shows a perspective cross-sectional view of a preferred embodiment of a sterilant challenge device for use in a steam sterilizer according to the present disclosure, while FIG. 2 shows a partial cross-sectional side view of the same. The sterilant challenge device is adapted for determining the efficacy of the non-condensable gas removal stage of the sterilization cycle andor the quality of steam sterilant in relation to its content of non-condensable gasgases. The device comprises a metal tube 1 having an inner bore 2 (see FIG. 2). The inner bore 2 of the metal tube 1 defines a free space which is open at an open end 8 (see FIG. 2) for the entry of sterilant and closed at the other closed end 11 (see FIG. 2). The device further comprises one or more thermal loads 3 located around the tube 1.

In the specific embodiment of FIG. 1 two thermal loads 3 are depicted. In the exemplary embodiment shown in FIG. 1 each thermal load 3 is provided with its respective temperature sensor 9. However, it may be sufficient to provide a single temperature sensor at only one thermal load; in this case desirably at a thermal load near the closed end of the metal tube. If more than two thermal loads are provided, one or more of the thermal loads may comprise a temperature sensor or each of the thermal loads may comprise a temperature sensor.

The metal tube 1, the thermal loads 3 and the temperature sensors 9 are provided within a housing 10 which is mounted on a base 12. The housing generally provides steam protection and typically the end of the housing opposite to the open end of the tube is closed (see FIG. 2). In FIG. 1, this closed end of the housing 10 was not been drawn to allow for ease in viewing of the interior of the housing. The housing 10 may include one or more inner housings 13 and 14 between the (outer) housing 10 and the metal tube, loads and temperature sensors. These inner housings may serve to thermally insulate the metal tube from the outside environment and to aid in limiting thermally influence to just over the open end of the tube. Typically the end of the inner housing opposite to the open end of the tube is closed (see FIG. 2), and once again for purposes of viewing, the closed ends of the inner housings 13 and 14 have been not been drawn in FIG. 1.

Figure 3A:
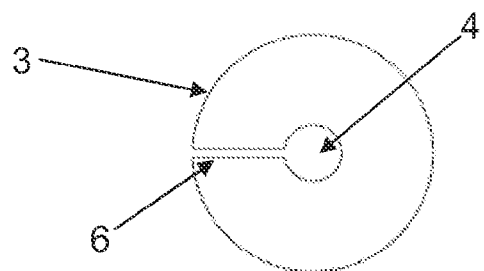
FIGS. 3a-3d shows various exemplary embodiments of a thermal load according to the present disclosure.

In the exemplary embodiment shown in FIGS. 1 and 2 the metal tube 1 is a hollow cylinder and the two thermal loads 3 have a shape substantially corresponding to a cylinder with a bore 4 (see FIG. 3a). The size and shape of the bore 4 of the thermal loads 3 essentially corresponds to the outer size and shape of the metal tube 1. Thus, a tight connection between the inner surface of the bore 4 of the thermal loads 3 on the one hand and the outer surface of the metal tube 1 on the other hand may be achieved which allows for a well-defined heat transfer between the tube and the thermal loads.

During use in a sterilization cycle, steam sterilant enters through the open end 8 of the metal tube 1 into the free space defined by the bore 2 of the metal tube 1. A portion of the steam sterilant condenses at the inner surface of the bore 2 of the metal tube 1 which leads to an increase of temperature of the thermal loads 3 due to condensation heat. This temperature increase is measured by means of the temperature sensors 9. The amount of temperature increase measured allows for calculation of the amount of steam condensed within the bore 2 of the metal tube 1 and consequently the volume of non-condensable gases formed at the top end of the bore 2 of the metal tube 1. The condensed steam sterilant flows down at the inner surface of the metal tube 1 forming water droplets at the open end 8 of the metal tube 1. In order to encourage the water droplets to drip off the edge of the open end 8 of the metal tube 1, a tapered open end 8 as shown in FIG. 2 is preferred. Due to the tapered end, condensed water will be drained down to and collected at the bottommost end of the tapered open end 8 of the metal tube 1, thus forming larger water droplets much quicker, which will then drip off the edge of the open end 8.

Preferably, the metal tube has a low thermal conductivity of 30 $Wm^{-1}K^{-1}$ or less, more preferably of 25 $Wm^{-1}K^{-1}$ or less, and most preferably of 20 $Wm^{-1}K^{-1}$ or less. The metal tube preferably has a thermal conductivity greater than 2 $Wm^{-1}K^{-1}$, more preferably greater than 4 $Wm^{-1}K^{-1}$. Suitable materials for the metal tube include stainless steel; non-rusting steel; CrNi-containing steel; titanium; and titanium alloys.

The thermal loads, on the other hand, preferably have a large heat capacity of preferably equal to or greater than 0.5 $Jg^{-1}K^{-1}$ at 25° C., more preferably of equal to or greater than 0.7 $Jg^{-1}K^{-1}$, even more preferably of equal to or greater than 0.85 $Jg^{-1}K^{-1}$. An exemplary suitable material for the thermal loads is aluminium.

Figure 3B:
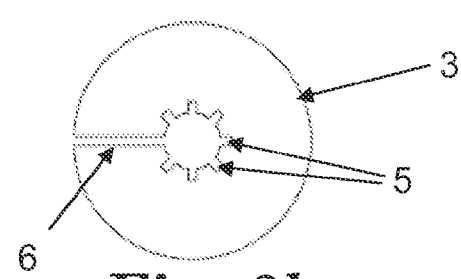

During the non-condensable gas removal stage of a sterilization cycle the metal tube 1 and the thermal loads 3 may exhibit different rates of expansioncontraction. In order to accommodate the stress involved the cylinder of the thermal load 3 preferably comprises a radial slit 6 (see FIG. 1 and in particular FIG. 3a) extending from the outer surface of the cylinder to the bore 4 of the cylinder. Such a slit is referred to in the following as an end-to-end slit. It is to be recognized that the end-to-end slit 6 in the illustrated embodiment is as such not visible in FIG. 2, because the cross-sectional slice runs through the gap formed by the slit. By expansion and compression of said slit 6 the thermal load 3 slightly flexes. While a single slit extending from the outer surface of the cylinder to the bore of the cylinder as shown in FIG. 3a may be sufficient, it may be desirable to provide one or more additional radial slits 7 which extend from the outer surface of the cylinder towards (but not extending to) the bore 4 of the cylinder as shown in FIG. 3d. In the event there are two or more radial slits, preferably they are spaced equidistantly from each other.

It is furthermore preferred that the bore 4 of the load 3 andor the surface of the bore 4 of the load 3 is shaped such as to only intermittently contact the metal tube 1. Thus, the amount of heat transfer between the tube and the load may be controlled and optimized. For example, the surface of the bore 4 of the load 3 may comprise at least one laterally or longitudinally extending groove 5, preferably two or more laterally andor longitudinally extending grooves 5 as shown in FIG. 3b. In essence, heat transfer only takes place at the intermittent contact between the load 3 and the tube 1 where no grooves 5 are present. Alternatively or in addition, a foil or sheet 15 of thermally insulating material may be provided between the metal tube 1 and the thermal load 3 as shown in FIG. 3c.

Figure 3C:
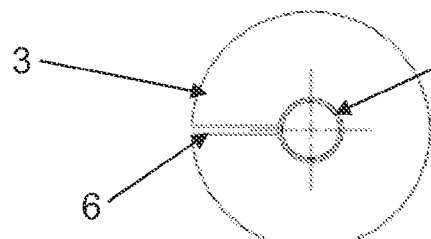
Figure 3D:
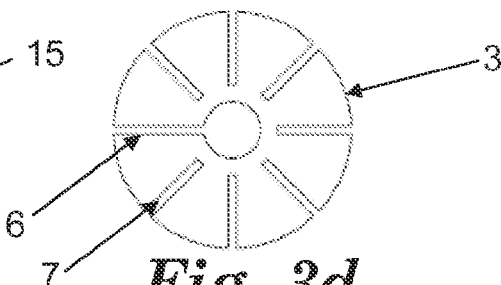

The different aspects shown in FIGS. 3a-3d may be combined with each other. For example, a plurality of grooves 5 as shown in FIG. 3b and a plurality of slits 6 as shown in FIG. 3d may be combined. Similarly, a plurality of slits 6 as shown in FIG. 3d may be combined with a foil or sheet 15 of thermally insulating material as shown in FIG. 3c. It will also be evident to the skilled person that the number and shape of the grooves and slits may be varied without departing from the scope of the present invention. Moreover, while a cylindrical thermal load 3 is preferred, the thermal load 3 does not necessarily have to be cylindrical, but its cross-section may also be elliptical, hexagonal, quadratic or the like.

It is, however, preferred that each thermal load, which substantially entirely surrounds the metal tube is provided as a single integral piece (apart from the end-to-end slit, if applicable),. Thermal loads may be mounted onto the tube by first cooling the tube and warming the load and then subsequently sliding and positioning the load onto the tube. Alternatively and more conveniently, the thermal load may comprise an end-to-end slit as described above. By means of a simple wedge the end-to-end slit (e.g. the slit 6 shown in FIG. 3a) may be slightly expanded thus increasing the diameter of the inner bore of the thermal load. The thermal load may then be easily slipped over the metal tube. Once the load is positioned at the right height of the metal tube, the wedge may be removed, thus decreasing the inner diameter of the bore of the thermal load which may thus tightly enclose the outer surface of the metal tube. Such thermal loads consisting of a single integral piece may be more easily mounted than the thermal loads known in the prior art. Ease in mounting, in particular expansion with a wedge during mounting, may be further facilitated by providing one or more radial slits from the outside towards the bore of the thermal load as described above.

The invention claimed is:

1. Sterilant challenge device for use in a steam sterilizer for determining the efficacy of the non-condensable gas removal stage of a sterilization cycle and/or the quality of steam sterilant in relation to its content of non-condensable gas(es), the device comprising:
    a metal tube (1) having a bore (2) defining a free space which is open at one end for the entry of sterilant and closed at the other end, wherein the metal tube is open to an outside environment; and
    at least one solid thermal load (3) located around the tube (1).

2. The device of claim 1, wherein the metal tube (1) has a thermal conductivity of 30 $Wm^{-1}K^{-1}$ or less.

3. The device of claim 2, wherein the metal tube (1) has a thermal conductivity of 2 $Wm^{-1}K^{-1}$ or more.

4. The device of claim 1, wherein the metal tube (1) has a length of 15 cm or less.

5. The device of claim 1, wherein the metal tube is a hollow cylinder having a wall thickness of 2 mm or less.

6. The device of claim 1, wherein the bore of the metal tube has a bore diameter of between 2 mm and 12 mm.

7. The device of claim 1, wherein the cross section of the metal tube has an area of 210 $mm^2$ or less.

8. The device of claim 1, wherein the material properties of the metal tube, in particular its thermal conductivity, are essentially isotropic.

9. The device of claim 1, wherein the metal tube comprises one or more selected from: stainless steel; non-rusting steel; CrNi-containing steel; titanium; and titanium alloys.

10. The device of claim 1, wherein the at least one load (3) has a bore (4).

11. The device of claim 10, wherein the size and shape of the bore (4) of the load generally corresponds to the outer size and shape of the metal tube (1).

12. The device of claim 10, wherein the bore (4) of the at least one load (3) and/or the surface of the bore of the at least one load is shaped such as to intermittently contact the metal tube (1).

13. The device of claim 10, wherein the surface of the bore (4) of the at least one load (3) comprises at least one laterally or longitudinally extending groove (5).

14. The device of claim 10, wherein the at least one load (3) has a shape substantially corresponding to a cylinder.

15. The device of claim 14, wherein the at least one load (3) comprises at least one radial slit (6) extending from the outer surface of the cylinder towards the bore (4) of the cylinder.

16. The device of claim 15, wherein the at least one load (3) comprises two or more radial slits (6) and said slits (6) are spaced equidistantly from each other.

17. The device of claim 1, wherein a foil or sheet (15) of thermally insulating material is provided between the tube and the at least one load.

18. The device of claim 17, wherein the foil or sheet (15) comprises a material comprising one or a combination of: polyester, polypropylene, polyacrylonitrile, Kapton, polyurethane, polyamide, polyimide, polyether imide, PTFE, polyvinylchloride, polycarbonate, epoxy resin, polymethylmethacrylate, polyethylene, and polystyrene.

19. The device of claim 17, wherein the foil or sheet (15) comprises a material having a thermal conductivity which is lower than that of the tube.

20. The device of clam 17, wherein the foil or sheet (15) comprises several holes and/or cut-outs to adjust the thermal coupling between the tube and the at least one load.

21. The device of claim 1, wherein the at least one load comprises or consists of aluminium.

22. The device of claim 1, wherein the open end (8) of the metal tube is tapered.

23. The device of claim 1, wherein the metal tube (1) is positioned such that, when exposed to steam sterilant, condensed steam sterilant flows down at an inner surface (2) of the metal tube and forms water droplets at the open end (8) of the metal tube (1).

24. The device of claim 1, further comprising:
a base (12), wherein the open end (8) of the metal tube (1) is adjacent to the base.

25. The device of claim 24, further comprising:
at least one housing (10) mounted to the base (12).

26. The device of claim 1, wherein each load from the at least one load comprises a temperature sensor (9).

27. The device of claim 26, wherein the temperature sensor (9) measures an increase of temperature of the at least one load (3).

28. The device of claim 26, wherein the device comprises a plurality of thermal loads located around the tube.

* * * * *

UNITED STATES PATENT AND TRADEMARK OFFICE
CERTIFICATE OF CORRECTION

PATENT NO. : 9,687,578 B2
APPLICATION NO. : 14/428457
DATED : June 27, 2017
INVENTOR(S) : Knut Schumacher et al.

It is certified that error appears in the above-identified patent and that said Letters Patent is hereby corrected as shown below:

In the Specification

Column 14
Line 6 (approx.), after "U.S.C." insert -- § --.
Line 17, delete "andor" and insert -- and/or --, therefor.
Line 47, delete "andor" and insert -- and/or --, therefor.

Column 2
Line 2, delete "andor" and insert -- and/or --, therefor.
Line 6, delete "andor" and insert -- and/or --, therefor.
Line 17, delete "airgas" and insert -- air/gas --, therefor.
Line 22, delete "airgas" and insert -- air/gas --, therefor.
Line 58, delete "9712637" and insert -- 97/12637 --, therefor.

Column 3
Line 2, delete "andor" and insert -- and/or --, therefor.
Line 21, delete "expansioncontraction" and insert -- expansion/contraction --, therefor.
Line 26, delete "expansioncontraction." and insert -- expansion/contraction. --, therefor.
Line 38, delete "andor" and insert -- and/or --, therefor.
Line 39, delete "gasgases." and insert -- gas/gases. --, therefor.
Line 58, delete "andor" and insert -- and/or --, therefor.

Column 4
Line 37, delete "andor" and insert -- and/or --, therefor.
Line 44, delete "andor" and insert -- and/or --, therefor.
Line 59, delete "andor" and insert -- and/or --, therefor.
Line 66, delete "andor" and insert -- and/or --, therefor.

Signed and Sealed this
Nineteenth Day of December, 2017

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,687,578 B2

Column 5
Line 16, delete "expansioncontraction" and insert -- expansion/contraction --, therefor.
Line 41, delete "andor" and insert -- and/or --, therefor.
Line 42-43, delete "gasgases." and insert -- gas/gases. --, therefor.

Column 6
Line 58, delete "expansioncontraction." and insert -- expansion/contraction. --, therefor.

Column 7
Line 10, delete "andor" and insert -- and/or --, therefor.
Line 16, delete "andor" and insert -- and/or --, therefor.